(12) United States Patent
Tsuji et al.

(10) Patent No.: US 9,476,767 B2
(45) Date of Patent: Oct. 25, 2016

(54) SPECTROMETRY DEVICE, LIQUID CHROMATOGRAPH, AND WAVELENGTH CALIBRATION METHOD OF SPECTROMETER

(71) Applicant: SHIMADZU CORPORATION, Kyoto-shi, Kyoto (JP)

(72) Inventors: Shinji Tsuji, Kyoto (JP); Hiroyuki Togo, Shiki (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 18 days.

(21) Appl. No.: 14/737,758

(22) Filed: Jun. 12, 2015

(65) Prior Publication Data

US 2015/0362366 A1 Dec. 17, 2015

(30) Foreign Application Priority Data

Jun. 16, 2014 (JP) ................. 2014-123453

(51) Int. Cl.
*G01J 3/28* (2006.01)
*G01J 3/18* (2006.01)
*G01N 30/74* (2006.01)
*G01N 21/33* (2006.01)

(52) U.S. Cl.
CPC .. *G01J 3/18* (2013.01); *G01J 3/28* (2013.01); *G01N 30/74* (2013.01); *G01J 2003/2866* (2013.01); *G01J 2003/2873* (2013.01); *G01N 21/33* (2013.01)

(58) Field of Classification Search
None
See application file for complete search history.

(56) References Cited

U.S. PATENT DOCUMENTS

| 4,669,878 A | * | 6/1987 | Meier | G01J 1/4257 356/319 |
| 5,886,157 A | * | 3/1999 | Guengerich | C12N 9/0077 435/189 |
| 2005/0156146 A1 | * | 7/2005 | Leveille | G01J 1/429 252/521.1 |

* cited by examiner

*Primary Examiner* — Kara E Geisel
*Assistant Examiner* — Shawn Decenzo
(74) *Attorney, Agent, or Firm* — Westerman, Hattori, Daniels & Adrian, LLP

(57) ABSTRACT

The wavelength of a spectrometer is calibrated by using a commercial Ho glass filter. The spectrometer includes a light source including a $D_2$ lamp and not including a mercury lamp, and a reference wavelength input unit for inputting, as a reference wavelength, a wavelength of a specific absorption peak separately measured for an Ho glass filter to be used. To calibrate the wavelength of the spectrometer by using the wavelength of a specific emission line peak of the $D_2$ lamp and the reference wavelength input by the reference wavelength input unit, the wavelength calibration unit holds a conversion table showing a theoretical relationship between the number of control pulses for rotating a diffraction element and the corresponding wavelength of diffracted light, and calibrates the number of control pulses from the conversion table by the wavelength calibration unit.

11 Claims, 10 Drawing Sheets

SPECTROMETRY DEVICE, LIQUID CHROMATOGRAPH, AND WAVELENGTH CALIBRATION METHOD OF SPECTROMETER

BACKGROUND OF THE INVENTION

1. Field of the Invention

The present invention relates to a spectrometry device, such as an ultraviolet-visible spectrophotometer (UV), that is used as an independent measurement device or as a detector of a measurement device such as a liquid chromatograph, a liquid chromatograph including the spectrometry device as a detector, and a wavelength calibration method of the spectrometer. The liquid chromatograph may be a high-performance liquid chromatograph.

2. Description of the Related Art

Some spectrometry devices include a diffraction grating as a wavelength dispersion element, and by rotating the diffraction grating, select the wavelength of diffracted light that is to emerge from an exit slit. A pulse motor for rotating the diffraction grating is provided, and a predetermined number of control pulses are sent from a control unit to the pulse motor to thereby rotate the diffraction grating by a predetermined angle and to select the wavelength of the diffracted light.

The wavelength of diffracted light to emerge from the exit slit and the number of control pulses for rotating the diffraction grating are theoretically determined in advance, and the control unit sends the number of control pulses corresponding to the target wavelength to the pulse motor.

Depending on the accuracy of attachment of the diffraction grating or the accuracy of processing of parts, a theoretically determined wavelength may not be obtained even if a predetermined number of control pulses are sent to the pulse motor. Thus, calibration is performed by using an emission line spectrum whose wavelength is known.

Calibration of the rotation position of the pulse motor for rotating the diffraction grating is performed, for example, by searching for an emission line in the spectrum of a deuterium ($D_2$) lamp and defining its position as a reference position 656.1 nm on the long-wavelength side, and searching for an emission line in the spectrum of a mercury lamp and defining its position as a reference position 253.7 nm on the short-wavelength side. The position of an emission line is already determined based on the physical quantity, and thus, there is no individual variability, and the reference positions for calibration do not change.

Use of the mercury lamp that is used for determining the reference position on the short-wavelength side will possibly be prohibited in the future due to restrictions by "Restriction of Hazardous Substances (RoHS)". Accordingly, as an alternative to the emission line wavelength of the mercury lamp, use of the peak wavelength of Ho absorption spectrum of a holmium (Ho) glass filter has been considered. The absorption peak of Ho is at 241.7 nm (NIST (National Institute of Standards and Technology, the United States of America) standard), and there is an attempt to use it as a reference absorption peak for determining the reference position on the short-wavelength side, in place of the emission line wavelength of the mercury lamp.

However, when measuring the absorption spectrum of a commercial Ho glass filter, it was found that the absorption peak at 241.7 nm as the reference absorption peak overlapped a large absorption peak, on the short-wavelength side, based on an additive for a substrate, and that the reference absorption peak position was shifted from 241.7 nm. Moreover, the shift amount was different for each commercial Ho glass filter.

An example is shown in FIG. 11. FIG. 11 shows the absorption spectra of three commercial Ho glass filters, and shows the range around 241.7 nm. Calibration is performed by the actual analysis device that measures the sample. Accordingly, measurement of the absorption spectrum is also performed by a spectrophotometer for sample measurement, and although the measurement bandwidth is great with the slit width of the exit slit being 8 mm, it is possible to determine the absorption peak wavelength. If the slit width of the exit slit is reduced and the measurement bandwidth is reduced, a sharp peak waveform may be obtained, but the amount of diffracted light transmitted to a cell for measurement is more reduced as the slit width of the exit slit is more reduced. Also, even if the peak waveform is sharp, the absorption peak wavelength of Ho is still affected by the absorption peak due to an additive for a substrate.

SUMMARY OF THE INVENTION

The present invention has its object to enable calibration of the wavelength of a spectrometer by using a commercial Ho glass filter and by using its specific absorption peak wavelength as the reference wavelength on the short-wavelength side.

A spectrometry device of the present invention includes a spectrometer and a wavelength calibration unit for calibrating the wavelength of the spectrometer. The spectrometer includes a diffraction element, a light source for generating incident light for the diffraction element, a light detection element arranged at a position for receiving light dispersed by the diffraction element, and a wavelength drive unit to be controlled by a control pulse to rotate the diffraction element with respect to an incident direction of the incident light.

In the spectrometer, the light source includes a $D_2$ lamp but not a mercury lamp. The emission line peak wavelength of the $D_2$ lamp is decided as a physical quantity. Unlike a conventional spectrometry device, the spectrometer does not include a mercury lamp to be used as a reference wavelength for wavelength calibration, and uses a specific absorption peak spectrum of an Ho glass filter instead of the emission line spectrum of a mercury lamp. To this end, a filter attachment unit for attaching an Ho glass filter in an attachable/detachable manner on a light path between the light source and the diffraction element is provided.

Since the wavelength of the absorption peak of Ho at 241.7 nm to be used for calibration, among the absorption peaks of the Ho glass filter, is different for each Ho glass filter, a reference wavelength input unit for inputting is provided, as a reference wavelength, a wavelength which has separately been measured for a specific absorption peak of a Ho glass filter to be used.

Moreover, the wavelength calibration unit is configured to calibrate the wavelength of the spectrometer by using a wavelength of a specific emission line peak of the $D_2$ lamp and the reference wavelength input by the reference wavelength input unit. The wavelength calibration unit includes a conversion table holding unit for holding a conversion table showing a theoretical relationship between the number of control pulses for rotating the diffraction element and a corresponding wavelength of diffracted light, and a control pulse number calibration unit for calibrating the number of control pulses from the conversion table.

The control pulse number calibration unit is configured to calibrate the number of control pulses from the conversion table based on the number of control pulses $n_{01}$ that is the number of control pulses obtained from the conversion table and that corresponds to a wavelength of a specific emission line peak of the $D_2$ lamp, the number of control pulses $n_{02}$ that is the number of control pulses obtained from the conversion table and that corresponds to the reference wavelength, the number of control pulses $n_1$ before calibration at a time of detection of the emission line peak of the $D_2$ lamp, and the number of control pulses $n_2$ before calibration at a time of detection of the specific absorption peak of the Ho glass filter.

A liquid chromatograph includes a liquid delivery unit, arranged at an upstream end of a flow path through which a mobile phase is to flow, for supplying the mobile phase, a sample injection unit for injecting a sample into the flow path, a separation column arranged on downstream of the sample injection unit, a flow cell, arranged on downstream of the separation column, through which an eluate from the separation column is to flow, and a spectrometry device arranged to optically detect the eluate flowing through the flow cell.

The liquid chromatograph of the present invention is characteristic in that it uses the spectrometry device of the present invention as the spectrometry device. In the spectrometry device, the flow cell is arranged on a light path from the diffraction element to the light detection element at the spectrometer.

A wavelength calibration method of the present invention is a wavelength calibration method for calibrating a wavelength of a spectrometer including a diffraction element, a light source for generating incident light for the diffraction element, a light detection element arranged at a position for receiving light dispersed by the diffraction element, and a wavelength drive unit for rotating the diffraction element based on the number of control pulses, where the light source including a $D_2$ lamp and not including a mercury lamp is used.

The wavelength calibration method of the present invention includes the following steps; specifically, the steps of:

attaching an Ho glass filter, at the spectrometer, on a light path between the light source and the diffraction element;

setting a specific absorption peak wavelength separately measured for the Ho glass filter as a reference wavelength;

holding a conversion table showing a theoretical relationship between the number of control pulses for rotating the diffraction element and a corresponding wavelength of diffracted light; and calibrating the number of control pulses from the conversion table based on the number of control pulses that is the number of control pulses obtained from the conversion table and that corresponds to a wavelength of a specific emission line peak of a $D_2$ lamp, the number of control pulses that is the number of control pulses obtained from the conversion table and that corresponds to the reference wavelength, the number of control pulses before calibration at a time of detection of the emission line peak of the $D_2$ lamp, and the number of control pulses before calibration at a time of detection of the absorption peak of the Ho glass filter.

According to the present invention, even if a mercury lamp is not used in addition to a $D_2$ lamp, an Ho glass filter is used instead of the mercury lamp, and the wavelength of a specific absorption peak separately measured for the Ho glass filter to be used is input as a reference wavelength, and the specific absorption peak of the Ho glass filter is detected and the peak wavelength is given as the input reference wavelength. Wavelength calibration for a spectrometer is performed in this manner by the $D_2$ lamp and the Ho glass filter, and thus, accurate calibration may be performed even when using varying Ho glass filters.

DETAILED DESCRIPTION OF THE INVENTION

Figure 1:
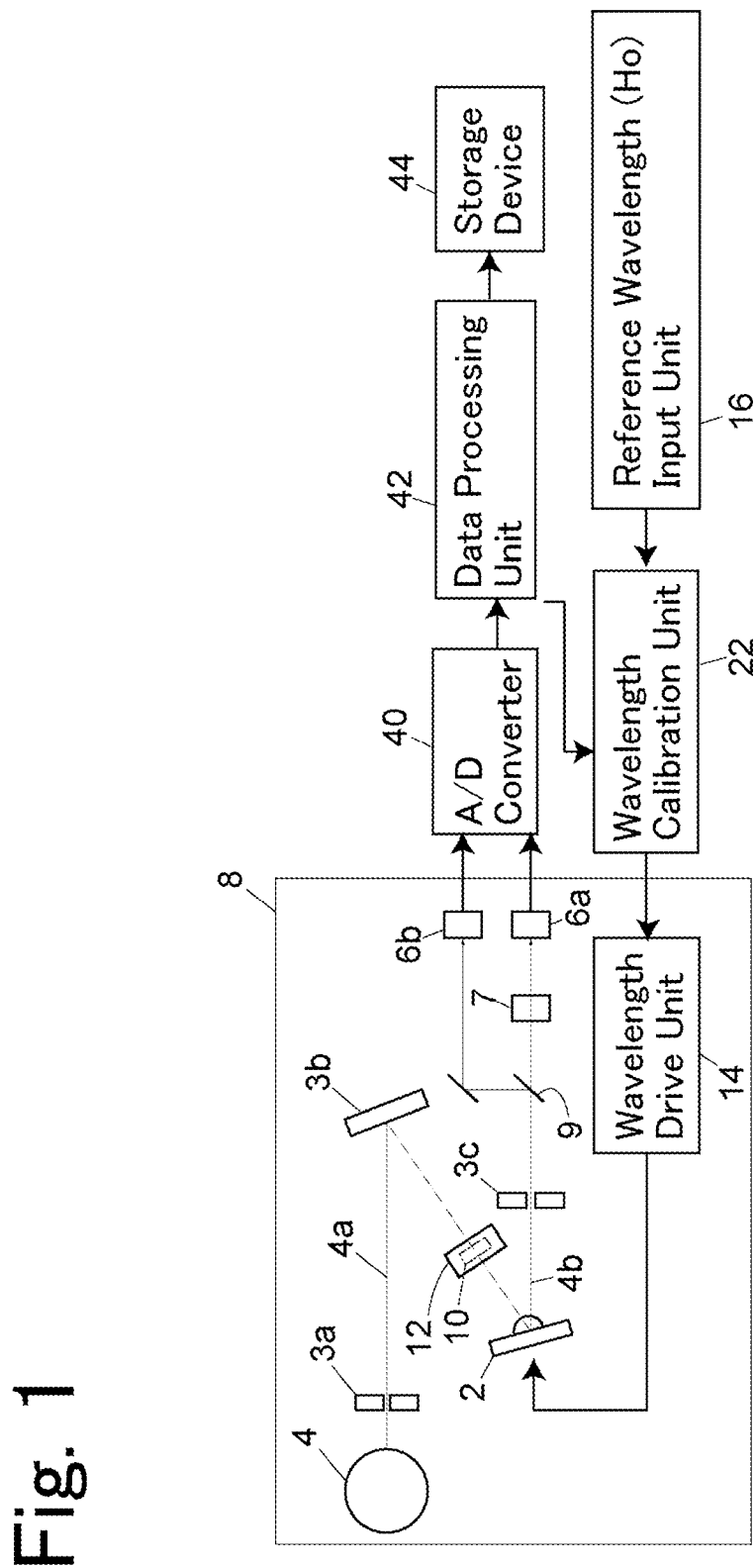
FIG. 1 is a schematic configuration diagram showing a spectrometry device of an embodiment.

FIG. 1 shows an embodiment of a spectrometry device. A spectrometer 8 includes a diffraction element 2, a $D_2$ lamp 4 as a light source of incident light for the diffraction element 2, light detection elements 6a and 6b arranged at positions for receiving light dispersed by the diffraction element 2, and a wavelength drive unit 14 for rotating the diffraction element 2 with respect to the incident direction of incident light. It is characteristic in that a mercury lamp is not provided as a light source, and it may be provided with only the $D_2$ lamp 4, or with the $D_2$ lamp and a tungsten lamp depending on the intended purpose. The $D_2$ lamp is used for sample measurement, and also for wavelength calibration.

At the spectrometer 8, light from the $D_2$ lamp 4 enters the diffraction element 2 via an entrance slit 3a, and light that is dispersed by the diffraction element 2 is output via an exit slit 3c. The diffraction element 2 is a plane diffraction grating, for example, and incident light 4a to the diffraction element 2 is to be imaged at the position of the entrance slit 3a by an optical element 3b that is schematically shown, and diffracted light 4b from the diffraction element 2 is to be imaged at the position of the exit slit 3c.

The wavelength drive unit 14 is provided to rotate the diffraction element 2 and to select the wavelength of light to be emitted from the exit slit 3c. The wavelength drive unit 14 rotates the diffraction element 2 with respect to the incident direction of the incident light 4a based on, at the time of wavelength calibration, the number of control pulses before calibration, and at the time of sample measurement, the number of control pulses after wavelength calibration.

A conventional spectrometer includes a mercury lamp for generating light of one reference wavelength for wavelength calibration, but the spectrometer of the present invention does not include a mercury lamp. An Ho glass filter 10 is used instead of a mercury lamp. The Ho glass filter 10 is used only at the time of wavelength calibration, and is not used at the time of sample measurement, and thus, the spectrometer 8 includes a filter attachment unit 12 for attaching the Ho glass filter 10 in an attachable/detachable manner on a light path between the light source 4 and the diffraction element 2.

A beam splitter 9 is arranged on a light path of diffracted light emitted from the exit slit 3c, and the light path is divided into two, and one is made the light path on the detection light side and the other is made the light path on the compensating light side. A cell 7 that is used at the time of measurement of a sample is arranged on the detection light side, and the light detection element 6a is arranged at the position for receiving the light transmitted through the cell 7. The light detection element 6b is arranged on the light path on the compensating light side. The light path on the compensating light side is used for measurement of absorbance of a sample.

As the cell 7, a cuvette or a flow cell is used depending on the analysis device in which the spectrometry device is used. The cell 7 is removed from the light path at the time of calibration, or in the case where it cannot be removed, the cell 7 is filled with pure water.

Detection signals of the light detection elements 6a and 6b are taken into a data processing unit 42 after being converted into digital signals by an A/D converter 40. At the time of sample measurement, the data processing unit 42 determines the absorbance at a predetermined wavelength, and stores the result in a storage device 44 or outputs it to the outside. At the time of calibration, detection of a specific emission line peak of the $D_2$ lamp and detection of a specific absorption peak set at a reference wavelength from the absorbance spectrum of the Ho glass filter 10 are performed. For example, as the emission line peak of the $D_2$ lamp, a wavelength of 656.1 nm is adopted. This wavelength does not change. On the other hand, as the Ho absorption peak, for example, a reference wavelength 241.7 nm according to NIST is adopted, but the absorption peak at this wavelength changes depending on an additive to the glass substrate.

For wavelength calibration, a wavelength calibration unit 22 and a reference wavelength input unit 16 are provided for inputting, to the wavelength calibration unit 22, as a reference wavelength value, an Ho absorption peak wavelength value which has been separately measured for an absorption peak set for a reference wavelength from the absorbance spectrum of the Ho glass filter 10.

Figure 2:
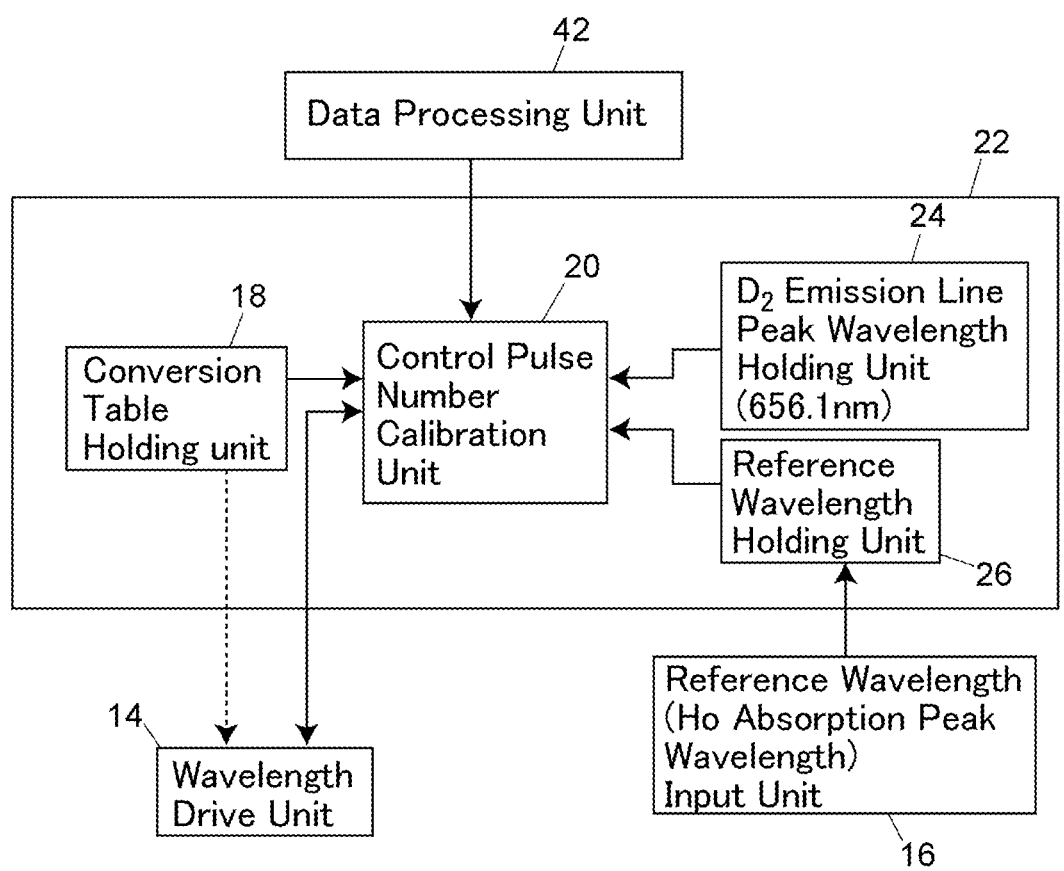
FIG. 2 is a block diagram showing a wavelength calibration unit according to the present embodiment.

As shown in FIG. 2, the wavelength calibration unit 22 includes a conversion table holding unit 18 for holding a conversion table showing a theoretical relationship between the number of control pulses for rotating the diffraction element 2 and the corresponding wavelength of diffracted light, and a control pulse number calibration unit 20. The wavelength calibration unit 22 is realized by a dedicated computer of the spectrometry device together with the data processing unit 42 and the storage device 44, or by a dedicated computer of a liquid chromatograph or other analysis device in which the spectrometry device is installed, or a general-purpose personal computer.

Figure 3:
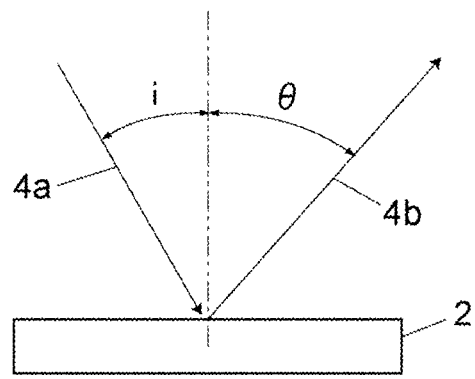
FIG. 3 is a diagram showing a relationship between an incident angle, an output angle and a diffraction wavelength of a plane diffraction grating.

As shown in FIG. 3, when the incident angle of the incident light 4a to the normal line of the diffraction grating 2 is given as i, and the reflection angle of the diffracted light 4b is given as θ, the following relationship is established:

$$Nm\lambda = \sin\theta - \sin i \quad (1).$$

N is the number of lines (l/mm) of the diffraction grating 2, m is the order, and λ is the spectral wavelength (nm) of the diffracted light. Since the positions of the entrance slit 3a and the exit slit 3c are fixed, the spectral wavelength λ of the diffracted light 4b is determined by rotating the diffraction grating 2 and changing the incident angle i and the reflection angle θ. The rotation angle of the diffraction grating 2 is decided by the number of pulses of the control pulse sent to the wavelength drive unit 14. The relationship determined by (1) described above, that is, the relationship between the number of control pulses for rotating the diffraction element 2 and the corresponding spectral wavelength λ, is held in the conversion table as data. This data shows the corresponding number of control pulses for each nanometer of the spectral wavelength λ, for example. To obtain a desired spectral wavelength λ, the corresponding number of control pulses is sent to the wavelength drive unit 14, and the pulse motor is driven and the diffraction grating 2 is rotated. This number of control pulses is the number of control pulses before calibration.

The control pulse number calibration unit 20 is configured to calibrate the number of control pulses in the conversion table based on two numbers of control pulses obtained from the conversion table, and the numbers of control pulses, before calibration, at the time of detection of a specific emission line peak of the $D_2$ lamp and a specific absorption peak of a specific Ho glass filter. The two numbers of control pulses obtained from the conversion table are the number of control pulses, obtained from the conversion table, corresponding to a specific emission line peak wavelength (656.1 nm) of the $D_2$ lamp, and the number of control pulses, obtained from the conversion table, corresponding to the reference wavelength input by the reference wavelength input unit 16. The numbers of control pulses before calibration at the time of detection of peaks are the numbers of control pulses before calibration that are sent to the wavelength drive unit 14 at the time of detection of respective peaks.

As an example, the wavelength calibration unit 22 includes a $D_2$ emission line peak wavelength holding unit 24 for holding a specific emission line peak wavelength (656.1 nm) of the $D_2$ lamp, and a reference wavelength holding unit 26 for holding the reference wavelength input by the reference wavelength input unit 16. In this case, the control pulse number calibration unit 20 is configured to obtain, from the conversion table, as the number of control pulses corresponding to a specific emission line peak wavelength of the $D_2$ lamp, the number of control pulses corresponding to the emission line peak wavelength held by the $D_2$ emission line peak wavelength holding unit 24, and to obtain, from the conversion table, as the number of control pulses corresponding to the reference wavelength, the number of control pulses corresponding to the reference wavelength held by the reference wavelength holding unit 26.

Figure 4:
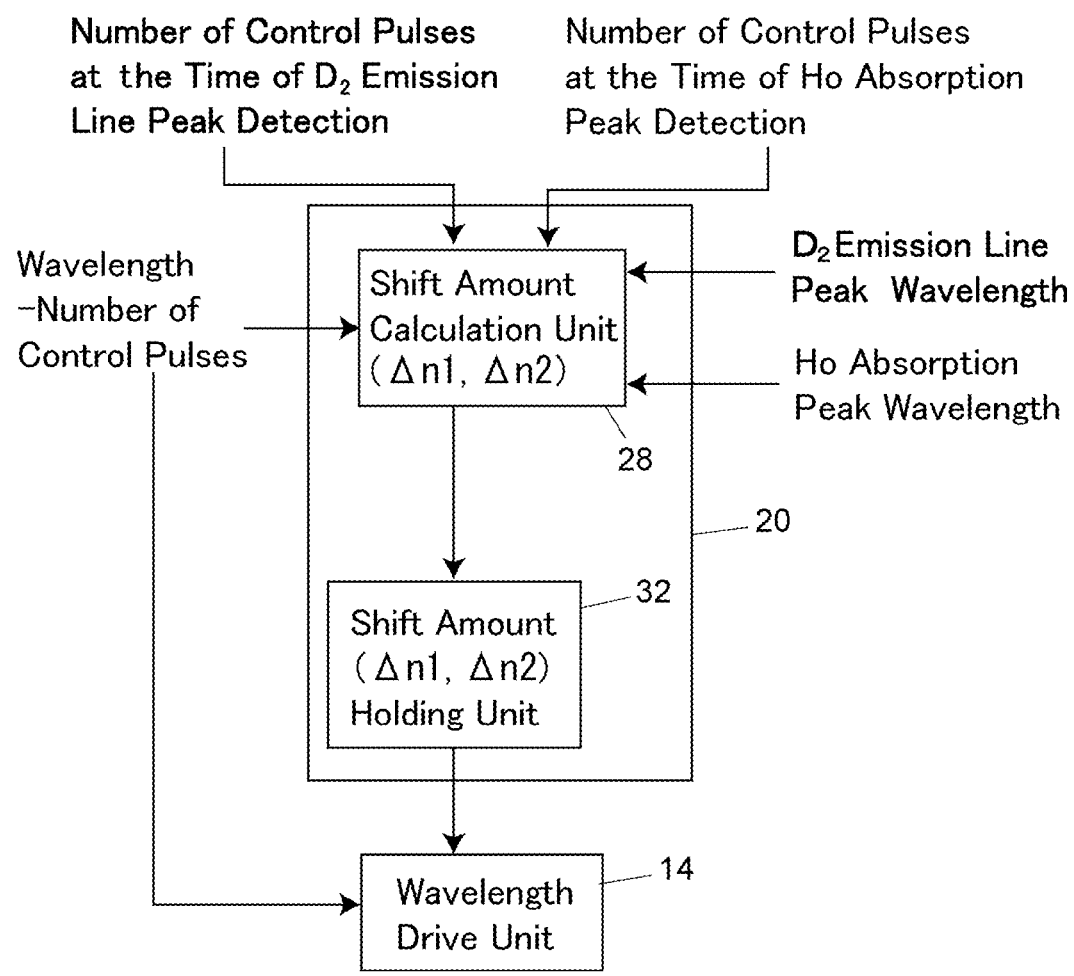
FIG. 4 is a block diagram showing a control pulse number calibration unit according to a first embodiment.

A first embodiment is shown in FIG. 4. The control pulse number calibration unit 20 is configured to include a shift amount calculation unit 28 and a shift amount holding unit 32.

The shift amount calculation unit 28 obtains the number of control pulses $n_{01}$ corresponding to the specific emission line peak wavelength of the $D_2$ lamp from the conversion table, and when the emission line peak of the $D_2$ lamp is detected, calculates a first shift amount $\Delta n_1$ at the emission line peak wavelength based on the number of control pulses $n_{01}$ and the number of control pulses $n_1$ before calibration at the time of detection of the emission line peak of the $D_2$ lamp, and obtains the number of control pulses $n_{02}$ corresponding to the reference wavelength from the conversion table, and calculates a second shift amount $\Delta n_2$ at the reference wavelength based on the number of control pulses $n_{02}$ and the number of control pulses $n_2$ before calibration at the time of detection of the absorption peak of the Ho glass filter corresponding to the reference wavelength.

The shift amount holding unit 32 holds the shift amounts $\Delta n_1$ and $\Delta n_2$ calculated by the shift amount calculation unit 28.

In this case, the wavelength drive unit 14 is configured to rotate the diffraction element 2 based on, at the time of wavelength calibration, the number of control pulses in the conversion table held by the conversion table holding unit 18, and at the time of sample measurement, the number of control pulses after wavelength calibration which is the number of control pulses held by the conversion table holding unit 18 after correction based on the shift amounts $\Delta n_1$ and $\Delta n_2$ held by the shift amount holding unit 32.

Figure 5:
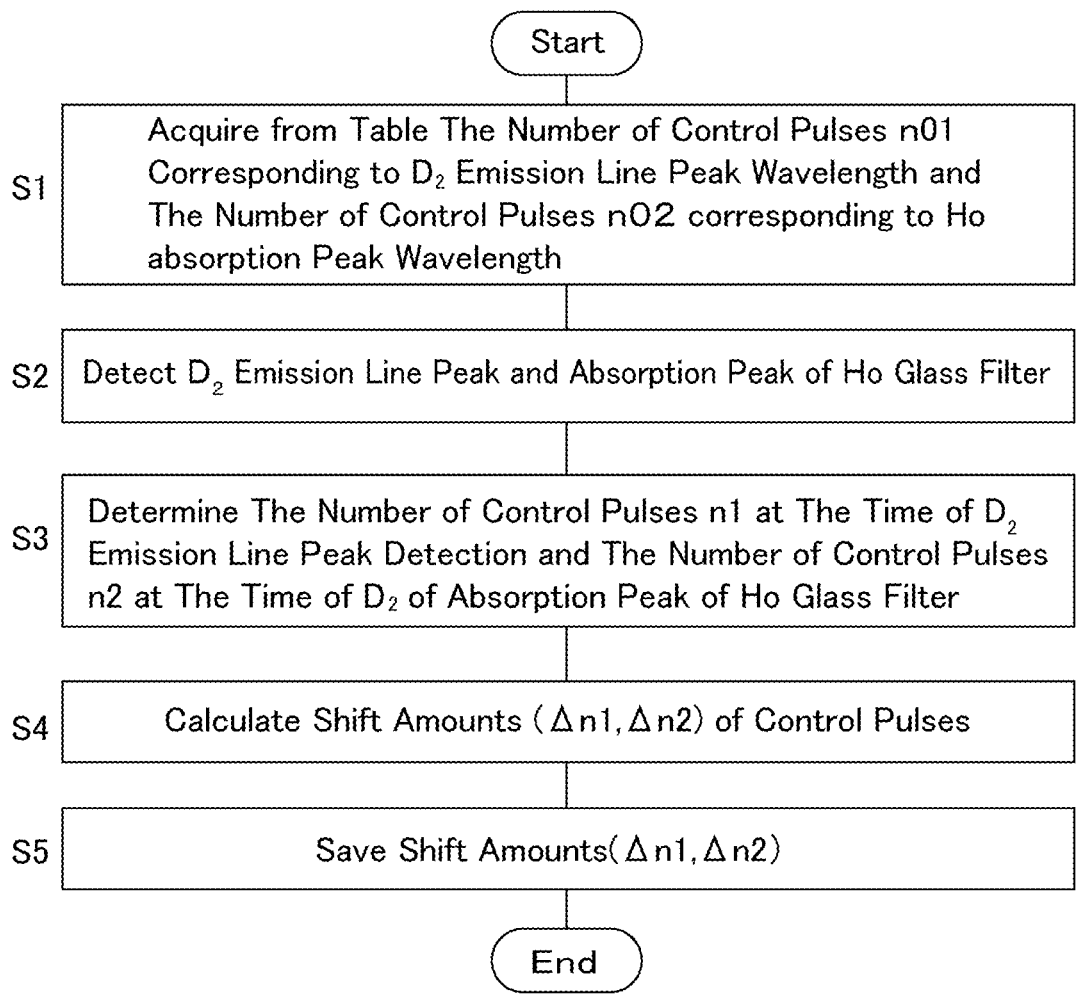
FIG. 5 is a flow chart showing a calibration operation according to the present embodiment.
Figure 6:
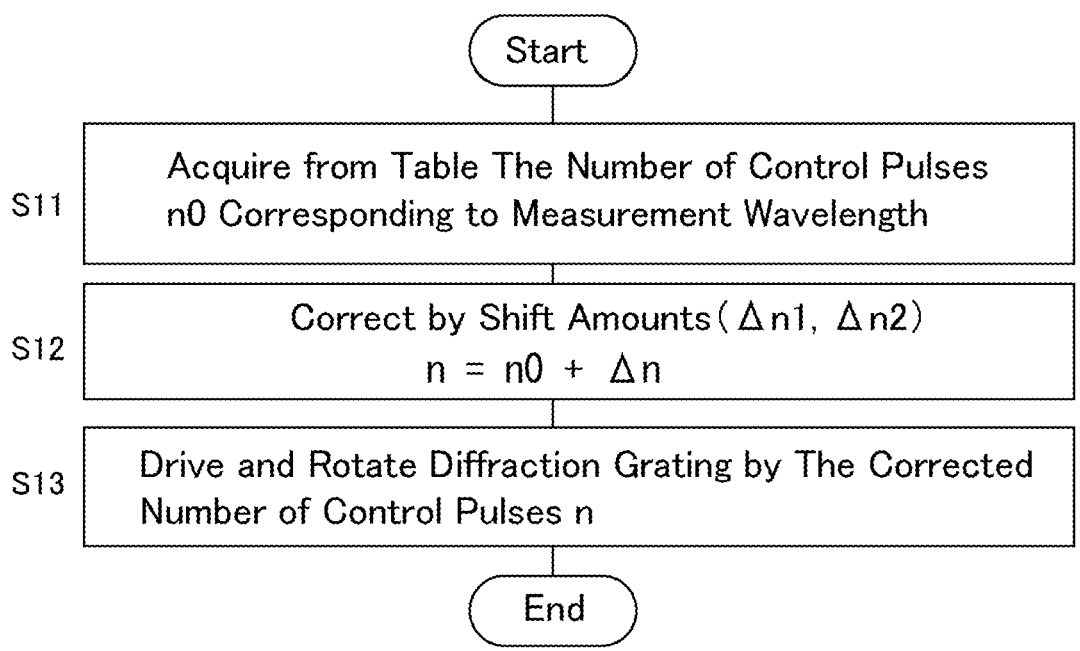
FIG. 6 is a flow chart showing a sample measurement operation according to the present embodiment.

An operation according to this embodiment is shown in FIGS. 5 and 6. FIG. 5 shows operations of the control pulse number calibration unit 20 and the wavelength drive unit 14 at the time of calibration. An Ho absorption peak wavelength value which has been separately measured for the Ho glass filter 10 is input and set as the reference wavelength, and a conversion table showing a theoretical relationship between the number of control pulses for rotating the diffraction element 2 and the corresponding wavelength of diffracted light is held in advance. At the spectrometer 8, the Ho glass filter 10 is attached on the light path between the light source 4 and the diffraction element 2. The timing of attaching the Ho glass filter 10 is not particularly specified as long as it is before detection of the Ho absorption peak.

The number of control pulses $n_{01}$ corresponding to a specific $D_2$ emission line peak wavelength (656.1 nm) and the number of control pulses $n_{02}$ corresponding to the reference wavelength of a specific Ho absorption peak are acquired from the conversion table in the conversion table holding unit 18 (step S1).

The emission line peak (656.1 nm) of the $D_2$ lamp 4 and the Ho absorption peak set at the reference wavelength (241.7 nm) are detected (step S2). To detect these peaks, the numbers of control pulses corresponding to respective peak wavelengths are acquired from the conversion table in the conversion table holding unit 18, and each number of control pulses is sent to the pulse motor of the wavelength drive unit 14 to rotate the diffraction element 2. At this stage, each of the numbers of control pulses is not calibrated, and thus, the corresponding peak may not be detected, but the peak may be detected by scanning of the corresponding approximate rotation position.

Detection of these peaks may be performed in a state where the Ho glass filter 10 is attached on the light path between the light source 4 and the diffraction element 2 at the spectrometer 8, and although detection of the Ho absorption peak cannot be performed unless the Ho glass filter 10 is attached, detection of the emission line peak of the $D_2$ lamp 4 may be performed in a state where the Ho glass filter 10 is not attached.

The numbers of control pulses $n_1$ and $n_2$ before calibration at the time of detecting, in step S2, the emission line peak of the $D_2$ lamp 4 and the Ho absorption peak, respectively, are determined (step S3). These numbers of control pulses $n_1$ and $n_2$ are the numbers of control pulses sent to the wavelength drive unit 14 at the time of detection of respective peaks, and when the control pulses are sent to the wavelength drive unit 14 from the wavelength calibration unit 22 or other control unit, these may be detected at the wavelength calibration unit 22 or other control unit, or at the wavelength drive unit 14 which has received the control pulses.

Either step S1 or S2 may be performed first.

Then, the first shift amount $\Delta n_1$ at the emission line peak wavelength is calculated based on the number of control pulses $n_{01}$ and the number of control pulses $n_1$, and the second shift amount $\Delta n_2$ at the reference wavelength is calculated based on the number of control pulses $n_{02}$ and the number of control pulses $n_2$ (step S4).

$$\Delta n_1 = n_1 - n_{01}$$

$$\Delta n_2 = n_2 - n_{02}$$

The calculated shift amounts $\Delta n_1$ and $\Delta n_2$ are saved (step S5).

FIG. 6 shows the operations of the control pulse number calibration unit 20 and the wavelength drive unit 14 at the time of sample measurement. The control pulse number calibration unit 20 acquires the number of control pulses n0 corresponding to a measurement wavelength from the conversion table (step S11).

This number of control pulses n0 is corrected by using the first shift amount $\Delta n_1$ at the emission line peak wavelength (656.1 nm) and the second shift amount $\Delta n_2$ at the reference wavelength (241.7 nm) that are held (step S12).

As the correction method, a linear interpolation method may be used, for example, to determine a shift amount $\Delta n$ at the measurement wavelength based on the shift amounts $\Delta n_1$ and $\Delta n_2$, and the calibrated number of control pulses n corresponding to the measurement wavelength may be determined by $$n = n0 + \Delta n.$$

The method of determining the calibrated number of control pulses n corresponding to the measurement wavelength is not limited to the linear interpolation method, and other methods may also be used. The method of calibrating an arbitrary wavelength based on two reference wavelengths is adopted by conventional devices that use the emission line peaks of a $D_2$ lamp and a mercury lamp, and the method adopted by these devices may also be used as the wavelength calibration method of the present embodiment.

The step of determining the calibrated number of control pulses n may be performed by the wavelength calibration unit 22 or by the wavelength drive unit 14.

The wavelength drive unit 14 drives the diffraction grating 2 to rotate by the corrected number of control pulses n (step S13).

Figure 7:
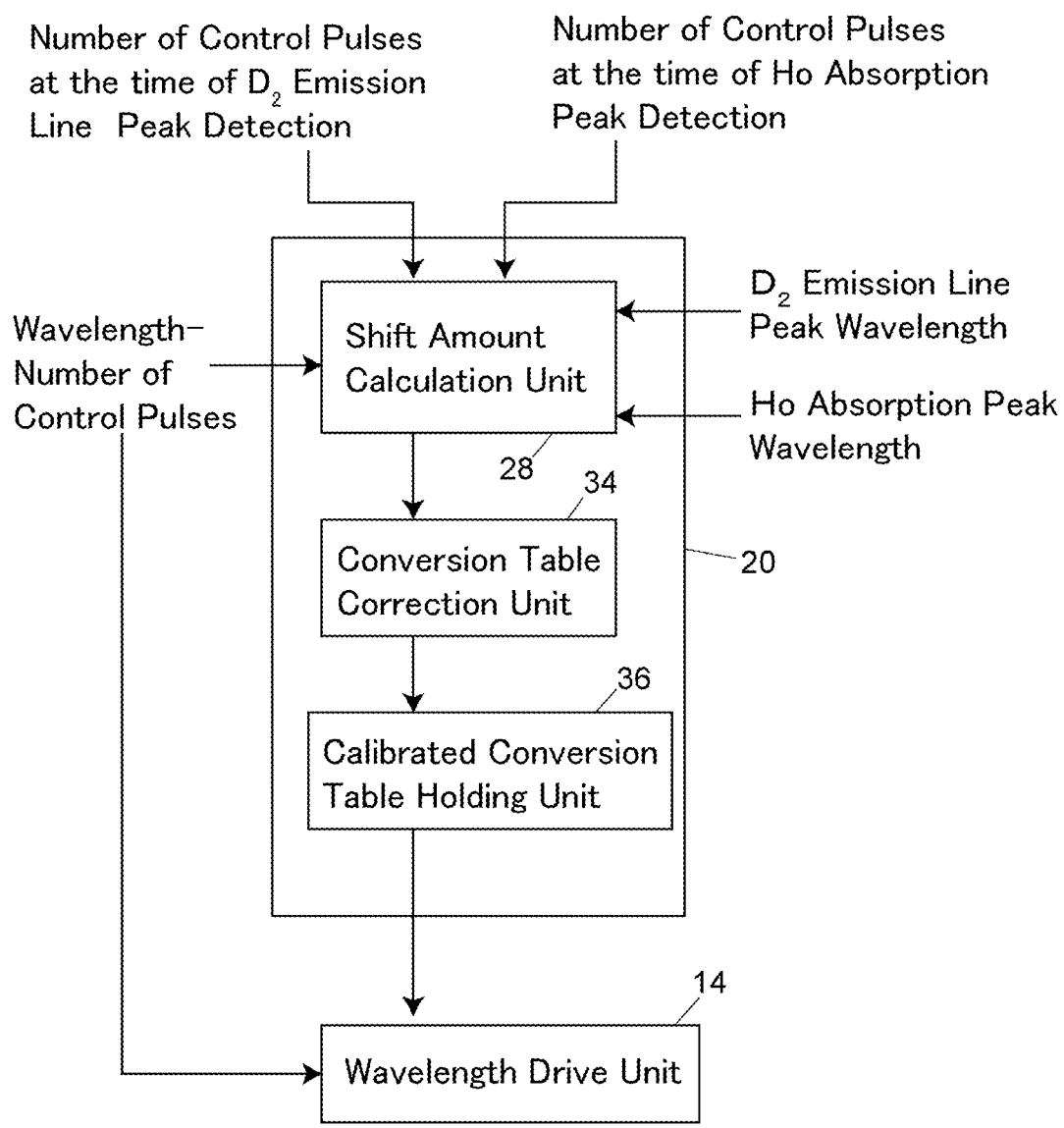
FIG. 7 is a block diagram showing a control pulse number calibration unit according to a second embodiment.

A second embodiment is shown in FIG. 7. The control pulse number calibration unit 20 is configured to include a shift amount calculation unit 28, a conversion table correction unit 34, and a calibrated conversion table holding unit 36.

The shift amount calculation unit 28 is the same as the one according to the first embodiment, and calculates the first shift amount $\Delta n_1$ at the emission line peak wavelength (656.1 nm) and the second shift amount $\Delta n_2$ at the reference wavelength (241.7 nm).

The conversion table correction unit 34 is configured to obtain a calibrated conversion table by correcting the number of control pulses in a conversion table by the shift amounts $\Delta n_1$ and $\Delta n_2$ calculated by the shift amount calculation unit 28. Also in this case, as the correction method, a linear interpolation method may be used, for example, to determine a shift amount $\Delta n$ at each wavelength based on the shift amounts $\Delta n_1$ and $\Delta n_2$, and the corrected number of control pulses n corresponding to each wavelength may be determined by $$n = n0 + \Delta n.$$

Also in this case, the method of determining the corrected number of control pulses n corresponding to each wavelength is not limited to the linear interpolation method, and other methods used as conventional calibration methods may also be used.

The calibrated conversion table holding unit 36 holds the calibrated conversion table which has been corrected by the conversion table correction unit 34.

In this case, the wavelength drive unit 14 is configured to rotate the diffraction element 2 with respect to the incident direction of the incident light based on, at the time of wavelength calibration, the number of control pulses in the conversion table before calibration that is held by the conversion table holding unit 18, and at the time of sample measurement, the number of control pulses in the calibrated conversion table that is held by the calibrated conversion table holding unit 36.

If the data in the conversion table before calibration indicates the number of control pulses corresponding to each nanometer of the spectral wavelength λ, for example, the calibrated conversion table will also indicate the number of control pulses corresponding to each nanometer of the spectral wavelength λ. The number of control pulses in the calibrated conversion table is the number of control pulses after calibration. To obtain a desired spectral wavelength λ after calibration, the corresponding number of control pulses is read from the calibrated conversion table and is sent to the wavelength drive unit 14, and the diffraction grating 2 is rotated.

Figure 8:
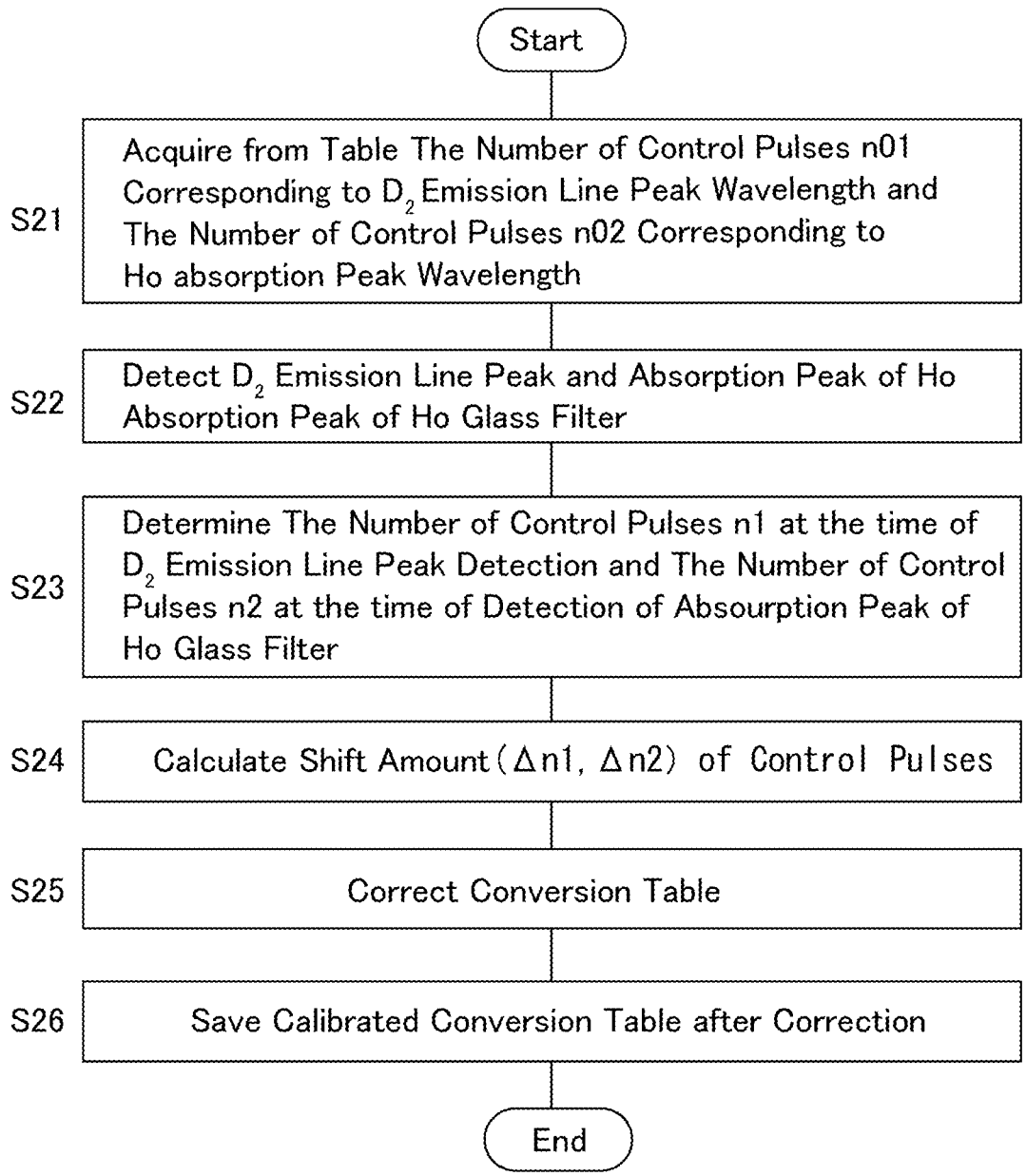
FIG. 8 is a flow chart showing a calibration operation according to the present embodiment.
Figure 9:
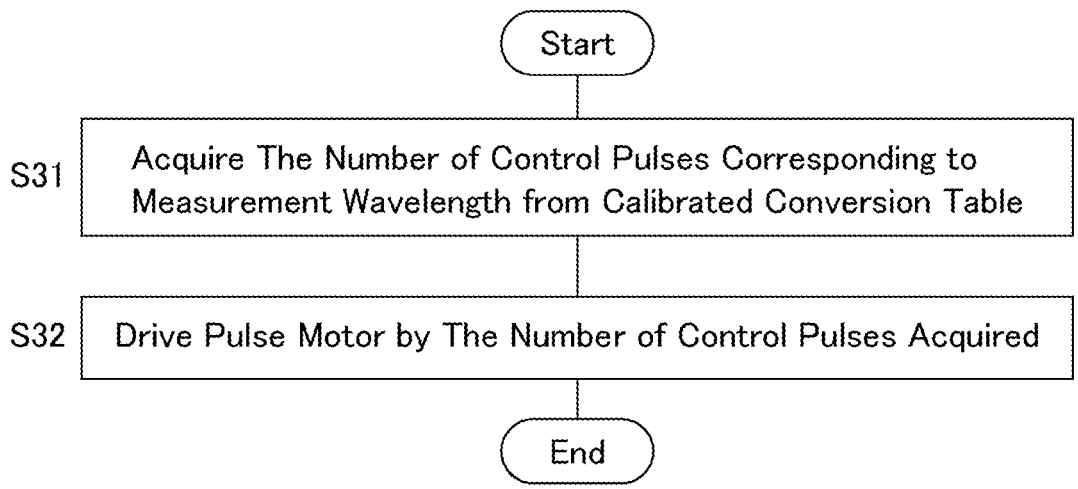
FIG. 9 is a flow chart showing a sample measurement operation according to the present embodiment.

The operation according to this embodiment is shown in FIGS. 8 and 9. FIG. 8 shows the operations of the control pulse number calibration unit 20 and the wavelength drive unit 14 at the time of calibration. As in the first embodiment, an Ho absorption peak wavelength which has been separately measured for the Ho glass filter 10 is input and set as the reference wavelength, and a conversion table, before calibration, showing a theoretical relationship between the number of control pulses for rotating the diffraction element 2 and the corresponding wavelength of diffracted light is held in advance. Also in this embodiment, the Ho glass filter 10 is attached on the light path between the light source 4 and the diffraction element 2 at the spectrometer 8, and as in the first embodiment, the timing of attaching the Ho glass filter 10 is not particularly specified as long as it is before detection of the Ho absorption peak.

The procedure of steps S21 to S24 of acquiring the number of control pulses $n_{01}$ corresponding to a specific $D_2$ emission line peak wavelength (656.1 nm) and the number of control pulses $n_{02}$ corresponding to the reference wavelength of a specific Ho absorption peak from the conversion table in the conversion table holding unit 18, detecting the emission line peak (656.1 nm) of the $D_2$ lamp 4 and the Ho absorption peak set at the reference wavelength (241.7 nm), determining the numbers of control pulses $n_1$ and $n_2$ before calibration at the time of detection of respective peaks, and calculating the first shift amount $\Delta n_1$ at the emission line peak wavelength and the second shift amount $\Delta n_2$ at the reference wavelength is the same as the procedure of steps S1 to S4 in FIG. 5 according to the first embodiment.

In the first embodiment, the control pulses for rotating the diffraction element is corrected by the shift amounts $\Delta n_1$ and $\Delta n_2$ at the time of sample measurement, but the present embodiment is different therefrom in that the number of control pulses in the conversion table is corrected in advance and is prepared in advance as the calibrated conversion table.

Accordingly, in this embodiment, the number of control pulses in the conversion table is corrected by the shift amounts $\Delta n_1$ and $\Delta n_2$ to thereby obtain the calibrated conversion table (step S24). As this method, the linear interpolation method as described above may be used, or other methods may be used.

The calibrated conversion table after correction is saved (step S25).

FIG. 9 shows the operations of the control pulse number calibration unit 20 and the wavelength drive unit 14 at the time of sample measurement. The control pulse number calibration unit 20 acquires the number of control pulses corresponding to the measurement wavelength from the calibrated conversion table (step S31).

The wavelength drive unit 14 drives the diffraction grating 2 to rotate by the number of control pulses acquired (step S32).

The spectrometry device of the present invention may be singularly used as an absorption spectrometer or as a detector of an analysis device.

Figure 10:
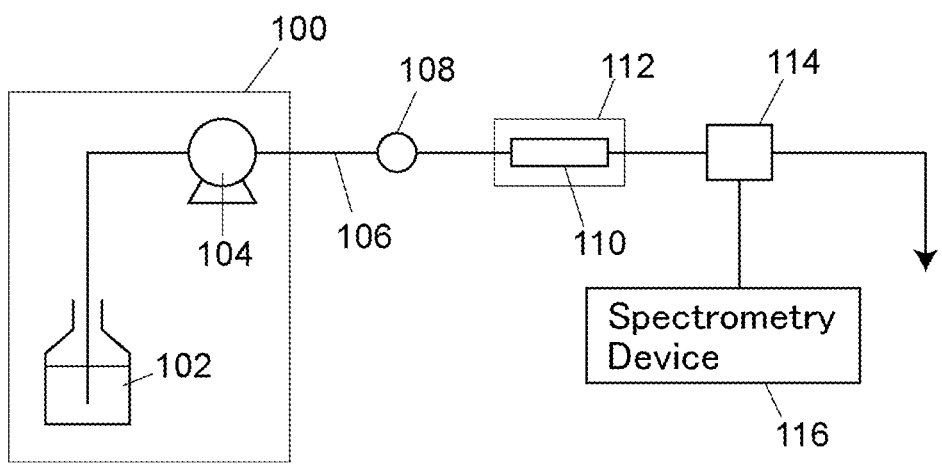
FIG. 10 is a schematic configuration diagram showing an example of a liquid chromatograph.
Figure 11:
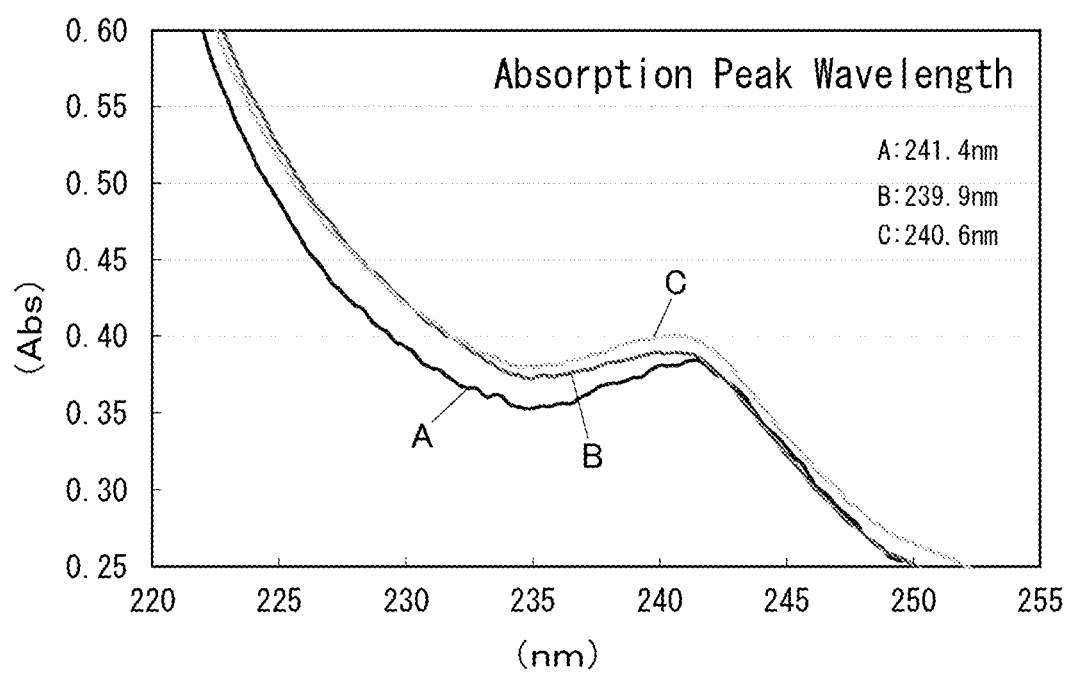
FIG. 11 shows absorption spectra of three commercial Ho glass filters, and shows peaks having absorption peak wavelengths at 241.7 nm and their periphery.

As an embodiment, a liquid chromatograph that uses a spectrometry device of an example as a detector is shown in FIG. 10.

A delivery unit 100 for supplying a mobile phase 102 is arranged at the upstream end of a flow path 106 through which the mobile phase 102 is to flow. The delivery unit 100 includes a delivery pump 104, and sends out the mobile phase into the flow path 106. The delivery unit 100 is shown schematically, and the number of mobile phases is not limited to one, and a case where a plurality of mobile phases are to be mixed, and a delivery unit for gradient analysis where the mixture ratio is changed over time are also possible.

A sample injection unit 108 for injecting a sample is arranged on the flow path 106. The sample injection unit 108 may be an automatic sample injection device (an autosampler). A separation column 110 is arranged downstream of the sample injection unit 108. The separation column 110 is accommodated in a column oven 112 for maintaining the same at a constant temperature.

A flow cell 114 through which an eluate from the separation column 110 is to flow is arranged downstream of the separation column 110. A spectrometry device 116 of an embodiment is arranged to optically detect the eluate flowing through the flow cell 114. The spectrometry device 116 is configured by including the spectrometer 8, the reference wavelength input unit 16, and the wavelength calibration unit 22 shown in FIG. 1, and the flow cell 114 is arranged at the position of the cell 7 at the spectrometer 8.

What is claimed is:
1. A spectrometry device comprising:
    a spectrometer including a diffraction element, a light source, including a $D_2$ lamp and not including a mercury lamp, for generating incident light for the diffraction element, a light detection element arranged at a position for receiving light dispersed by the diffraction element, and a wavelength drive unit to be controlled by a control pulse to rotate the diffraction element;
    a filter attachment unit, in the spectrometer, for attaching an Ho glass filter in an attachable/detachable manner on a light path between the light source and the diffraction element;
    a reference wavelength input unit for inputting, as a reference wavelength, a wavelength of a specific absorption peak separately measured for the Ho glass filter; and a wavelength calibration unit including a conversion table holding unit for holding a conversion table showing a theoretical relationship between the number of control pulses for rotating the diffraction element and a corresponding wavelength of diffracted light, and a control pulse number calibration unit for calibrating the number of control pulses from the conversion table based on the number of control pulses $n_{01}$ that is the number of control pulses obtained from the conversion table and that corresponds to a wavelength of a specific emission line peak of the $D_2$ lamp, the number of control pulses $n_{02}$ that is the number of control pulses obtained from the conversion table and that corresponds to the reference wavelength input by the reference wavelength input unit, the number of control pulses $n_1$ before calibration at a time of detection of the emission line peak of the $D_2$ lamp, and the number of control pulses $n_2$ before calibration at a time of detection of the absorption peak of the Ho glass filter.

2. The spectrometry device according to claim 1,
wherein the wavelength calibration unit includes a $D_2$ emission line peak wavelength holding unit for holding the wavelength of the emission line peak of the $D_2$ lamp, and a reference wavelength holding unit for holding the reference wavelength input by the reference wavelength input unit, and
wherein the control pulse number calibration unit is configured to use, at a time of obtaining the number of control pulses from the conversion table, an emission line peak wavelength held by the $D_2$ emission line peak wavelength holding unit and the reference wavelength held by the reference wavelength holding unit.

3. The spectrometry device according to claim 2,
wherein the control pulse number calibration unit includes
a shift amount calculation unit for calculating a first shift amount $\Delta n_1$ at the emission line peak wavelength based on the number of control pulses $n_{01}$, in the conversion table, corresponding to the emission line peak wavelength and the number of control pulses $n_1$ before calibration at a time of detection of the emission line peak of the $D_2$ lamp, and for calculating a second shift amount $\Delta n_2$ at the reference wavelength based on the number of control pulses $n_{02}$, in the conversion table, corresponding to the reference wavelength and the number of control pulses $n_2$ before calibration at a time of detection of the absorption peak, and
a shift amount holding unit for holding the shift amounts $\Delta n_1$ and $\Delta n_2$ calculated by the shift amount calculation unit, and
wherein the wavelength drive unit is configured to rotate the diffraction element based on, at a time of wavelength calibration, the number of control pulses in the conversion table held by the conversion table holding unit, and at a time of sample measurement, the number of control pulses after wavelength calibration that is the number of control pulses held by the conversion table holding unit after correction based on the shift amounts $\Delta n_1$ and $\Delta n_2$ held by the shift amount holding unit.

4. The spectrometry device according to claim 1,
wherein the control pulse number calibration unit includes
a shift amount calculation unit for calculating a first shift amount $\Delta n_1$ at the emission line peak wavelength based on the number of control pulses $n_{01}$, in the conversion table, corresponding to the emission line peak wavelength and the number of control pulses $n_1$ before calibration at a time of detection of the emission line peak of the $D_2$ lamp, and for calculating a second shift amount $\Delta n_2$ at the reference wavelength based on the number of control pulses $n_{02}$, in the conversion table, corresponding to the reference wavelength and the number of control pulses $n_2$ before calibration at a time of detection of the absorption peak, and
a shift amount holding unit for holding the shift amounts $\Delta n_1$ and $\Delta n_2$ calculated by the shift amount calculation unit, and
wherein the wavelength drive unit is configured to rotate the diffraction element based on, at a time of wavelength calibration, the number of control pulses in the conversion table held by the conversion table holding unit, and at a time of sample measurement, the number of control pulses after wavelength calibration that is the number of control pulses held by the conversion table holding unit after correction based on the shift amounts $\Delta n_1$ and $\Delta n_2$ held by the shift amount holding unit.

5. The spectrometry device according to claim 1,
wherein the control pulse number calibration unit includes
a shift amount calculation unit for calculating a first shift amount $\Delta n_1$ at the emission line peak wavelength based on the number of control pulses $n_{01}$, in the conversion table, corresponding to the emission line peak wavelength and the number of control pulses $n_1$ before calibration at a time of detection of the emission line peak of the $D_2$ lamp, and for calculating a second shift amount $\Delta n_2$ at the reference wavelength based on the number of control pulses $n_{02}$, in the conversion table, corresponding to the reference wavelength and the number of control pulses $n_2$ before calibration at a time of detection of the absorption peak,
a conversion table correction unit for calibrating the number of control pulses in the conversion table by the shift amounts $\Delta n_1$ and $\Delta n_2$ calculated by the shift amount calculation unit, and
a calibrated conversion table holding unit for holding a calibrated conversion table calibrated by the conversion table correction unit, and
wherein the wavelength drive unit is configured to rotate the diffraction element based on, at a time of wavelength calibration, the number of control pulses in the conversion table held by the conversion table holding unit, and at a time of sample measurement, the number of control pulses in the calibrated conversion table held by the calibrated conversion table holding unit.

6. The spectrometry device according to claim 2,
wherein the control pulse number calibration unit includes
a shift amount calculation unit for calculating a first shift amount $\Delta n_1$ at the emission line peak wavelength based on the number of control pulses $n_{01}$, in the conversion table, corresponding to the emission line peak wavelength and the number of control pulses $n_1$ before calibration at a time of detection of the emission line peak of the $D_2$ lamp, and for calculating a second shift amount $\Delta n_2$ at the reference wavelength based on the number of control pulses $n_{02}$, in the conversion table, corresponding to the reference wavelength and the number of control pulses $n_2$ before calibration at a time of detection of the absorption peak,
a conversion table correction unit for calibrating the number of control pulses in the conversion table by the shift amounts $\Delta n_1$ and $\Delta n_2$ calculated by the shift amount calculation unit, and a calibrated conversion table holding unit for holding a calibrated conversion table calibrated by the conversion table correction unit, and wherein the wavelength drive unit is configured to rotate the diffraction element based on, at a time of wavelength calibration, the number of control pulses in the conversion table held by the conversion table holding unit, and at a time of sample measurement, the number of control pulses in the calibrated conversion table held by the calibrated conversion table holding unit.

7. A liquid chromatograph comprising:
a delivery unit, arranged at an upstream end of a flow path through which a mobile phase is to flow, for supplying the mobile phase;
a sample injection unit for injecting a sample into the flow path;
a separation column arranged downstream of the sample injection unit;
a flow cell, arranged downstream of the separation column, through which an eluate from the separation column is to flow; and
the spectrometry device according to claim 1, the spectrometry device being arranged to optically detect the eluate flowing through the flow cell, the flow cell being arranged on a light path from the diffraction element to the light detection element at the spectrometer.

8. A liquid chromatograph comprising:
a delivery unit, arranged at an upstream end of a flow path through which a mobile phase is to flow, for supplying the mobile phase;
a sample injection unit for injecting a sample into the flow path;
a separation column arranged downstream of the sample injection unit;
a flow cell, arranged downstream of the separation column, through which an eluate from the separation column is to flow; and
the spectrometry device according to claim 2, the spectrometry device being arranged to optically detect the eluate flowing through the flow cell, the flow cell being arranged on a light path from the diffraction element to the light detection element at the spectrometer.

9. A liquid chromatograph comprising:
a delivery unit, arranged at an upstream end of a flow path through which a mobile phase is to flow, for supplying the mobile phase;
a sample injection unit for injecting a sample into the flow path;
a separation column arranged downstream of the sample injection unit;
a flow cell, arranged downstream of the separation column, through which an eluate from the separation column is to flow; and
the spectrometry device according to claim 3, the spectrometry device being arranged to optically detect the eluate flowing through the flow cell, the flow cell being arranged on a light path from the diffraction element to the light detection element at the spectrometer.

10. A liquid chromatograph comprising:
a delivery unit, arranged at an upstream end of a flow path through which a mobile phase is to flow, for supplying the mobile phase;
a sample injection unit for injecting a sample into the flow path;
a separation column arranged downstream of the sample injection unit;
a flow cell, arranged downstream of the separation column, through which an eluate from the separation column is to flow; and
the spectrometry device according to claim 4, the spectrometry device being arranged to optically detect the eluate flowing through the flow cell, the flow cell being arranged on a light path from the diffraction element to the light detection element at the spectrometer.

11. A wavelength calibration method for calibrating a wavelength of a spectrometer including a diffraction element, a light source for generating incident light for the diffraction element, a light detection element arranged at a position for receiving light dispersed by the diffraction element, and a wavelength drive unit for rotating the diffraction element with respect to an incident direction of the incident light based on the number of control pulses, the method comprising the steps of:
attaching an Ho glass filter, in the spectrometer, on a light path between the light source and the diffraction element;
setting an Ho absorption peak wavelength separately measured for the Ho glass filter as a reference wavelength;
holding a conversion table showing a theoretical relationship between the number of control pulses for rotating the diffraction element and a corresponding wavelength of diffracted light; and
calibrating the number of control pulses from the conversion table based on the number of control pulses that is the number of control pulses obtained from the conversion table and that corresponds to a wavelength of a specific emission line peak of a $D_2$ lamp, the number of control pulses that is the number of control pulses obtained from the conversion table and that corresponds to the reference wavelength, the number of control pulses before calibration at a time of detection of the emission line peak of the $D_2$ lamp, and the number of control pulses before calibration at a time of detection of the absorption peak of the Ho glass filter,
wherein the light source including a $D_2$ lamp and not including a mercury lamp is used.

* * * * *